(12) United States Patent
Johns et al.

(10) Patent No.: US 10,975,288 B2
(45) Date of Patent: Apr. 13, 2021

(54) ROBUST FLASH CALCULATION ALGORITHM FOR MICROEMULSION PHASE BEHAVIOR

(71) Applicant: THE PENN STATE RESEARCH FOUNDATION, University Park, PA (US)

(72) Inventors: Russell T. Johns, University Park, PA (US); Saeid Khorsandi Kouhanestani, University Park, PA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 0 days.

(21) Appl. No.: 16/327,993

(22) PCT Filed: Aug. 25, 2017

(86) PCT No.: PCT/US2017/048727
§ 371 (c)(1),
(2) Date: Feb. 25, 2019

(87) PCT Pub. No.: WO2018/039630
PCT Pub. Date: Mar. 1, 2018

(65) Prior Publication Data
US 2019/0225870 A1 Jul. 25, 2019

Related U.S. Application Data

(60) Provisional application No. 62/379,511, filed on Aug. 25, 2016.

(51) Int. Cl.
*C09K 8/584* (2006.01)
*G06F 30/20* (2020.01)
(Continued)

(52) U.S. Cl.
CPC .......... *C09K 8/584* (2013.01); *G01N 33/2823* (2013.01); *G06F 17/18* (2013.01); *G06F 30/20* (2020.01)

(58) Field of Classification Search
CPC .......... E21B 43/16; E21B 43/26; E21B 43/34; C09K 8/584; C09K 8/602; C09K 3/00;
(Continued)

(56) References Cited

U.S. PATENT DOCUMENTS

2011/0246164 A1  10/2011  Gullapalli
2014/0069168 A1   3/2014  Frisby
(Continued)

OTHER PUBLICATIONS

Written Opinion of the International Search Authority issued in PCT/US2017/048727 dated Nov. 7, 2017.
(Continued)

*Primary Examiner* — Zakiya W Bates
(74) *Attorney, Agent, or Firm* — Troutman Pepper Hamilton Sanders LLP; Christopher C. Close, Jr.

(57) ABSTRACT

The technology extends hyperbolic-lipophilic difference and net average curvature (HLD-NAC) to a robust algorithm for predicting the phase behavior of microemulsions at different conditions away from experimental results. The HLD-NAC equations are modified to ensure consistency over the entire composition space including type II– and II+ regions. The algorithm converges and provides continuous estimates with any formation variable of tie lines and triangles for all Winsor types. The algorithm is configured such that discontinuities are eliminated and limiting tie lines near critical points are determined analytically. The algorithm is tuned using several sets of experimental data and provides for predictability of tie lines and tie triangles, and solubilization ratios.

7 Claims, 11 Drawing Sheets

(51) Int. Cl.
   *G01N 33/28*    (2006.01)
   *G06F 17/18*    (2006.01)
   *E21B 43/16*    (2006.01)
   *E21B 43/22*    (2006.01)

(58) Field of Classification Search
   CPC . C09K 8/86; C09K 8/588; C09K 8/68; C09K 8/92; C09K 8/52
   See application file for complete search history.

(56) References Cited

U.S. PATENT DOCUMENTS

| | | |
|---|---|---|
| 2014/0073541 A1 | 3/2014 | Ravikiran |
| 2014/0260659 A1 | 9/2014 | Sheila-Vadde |
| 2015/0073762 A1 | 3/2015 | Patacchini |

OTHER PUBLICATIONS

International Search Report issued in PCT/US2017/048727 dated Nov. 7, 2017.

ROBUST FLASH CALCULATION ALGORITHM FOR MICROEMULSION PHASE BEHAVIOR

CROSS-REFERENCE TO RELATED APPLICATION

This application is the U.S. National Phase under 35 U.S.C. § 371 of International Application No. PCT/US2017/048727 filed Aug. 25, 2017, which claims the benefit of U.S. Provisional Application No. 62/379,511 filed Aug. 25, 2016, the entire disclosure of which is hereby incorporated by reference herein.

TECHNICAL FIELD

The preset disclosure relates to the extension of hyperbolic-lipophilic difference and net and average curvature (HLD-NAC) to a robust algorithm to predict the phase behavior of a microemulsion at different conditions away from experimental results.

BACKGROUND

Surfactants can be useful in a variety of industrial and scientific applications (e.g., enhanced oil recovery, fracturing cleanup, cosmetics, cleaning, etc.) that require formation of a microemulsion phase, i.e., a clear, thermodynamically stable, isotropic liquid mixture of oil, water and surfactant. Some applications require efficient oil-component separation from the microemulsion phase and/or brine phase, while others may require the formation of a single microemulsion phase. For example, a well-designed surfactant-polymer (SP) flood can be useful as an enhanced oil recovery method to achieve high oil recovery when the reservoir displacements form three phases (microemulsion, brine and oil) at optimum conditions, i.e. the interfacial tensions (IFT) are reduced to ultra-low values below $10^{-3}$ dyne/cm. IFT is correlated to phase compositions and the microemulsion phase behavior is a function of surfactant properties, temperature, brine composition, oil composition and pressure. Other applications such as cleanup of hydraulic fracturing may require formation of only a single microemulsion phase so that oil and brine at the well "sandface" are extracted. These parameters can vary spatially and temporally in an oil field reservoir, but not all of them are typically accounted for in current phase behavior models. Further, current models used for enhanced oil recovery (EOR) either ignore the details of the microemulsion phase or use Hand's model to describe microemulsion phase behavior. In some cases, the Hand's coefficients are adjusted as a function of salinity, temperature, pressure, or oil composition. The Hand's model parameters, however, are not directly related to physical properties of surfactants so that adjustments are ad hoc and give limited predictive ability outside the range of the tuned data. Therefore, a predictive compositional phase behavior model for a wide range of conditions is an essential part of any surfactant application.

Microemulsion phase behavior is especially complex to model because of intermolecular and inter-micellar forces that control microemulsion phase behavior, and until this invention has not been achieved over the entire range of formulation parameters and compositions. The complexity is further increased by the numerous types of surfactant molecules used, and varying brine compositions present. Winsor defined four types of microemulsions based on the structure of micelles, and the composition of excess phases; type II−, II+, III, and IV. The Winsor types are qualitatively described based on affinity of the surfactant to water and oil phases.

There are three main ways surfactant affinity is described in the literature. Griffin used the size and strength of the hydrophilic and lipophilic groups in the surfactant to define the hydrophilic-lipophilic balance (HLB). This affinity, however, is a function of many parameters other than surfactant selection, including temperature, pressure, water composition and oil composition. Winsor defined the R-ratio to account for the overall effect of molecular forces at the interface on surfactant affinity. The R-ratio, however, is difficult to measure and calculate. Salager et al. made a significant and practical advance by defining the hydrophilic-lipophilic difference (HLD) based on the change in molar excess Gibbs free energy involved in the transfer of a surfactant molecule from the excess water phase to the excess oil phase. HLD is correlated to the fluid properties such as water and oil composition, temperature and surfactant properties. A positive HLD means that the surfactant prefers oil, while a negative value indicates it prefers brine. HLD equal to negative infinity, for example, leads to a surfactant that is completely miscible with brine, but immiscible with oil, while the reverse is true for positive infinity.

Troncoso and Acosta used the UNIFAC model to predict activity coefficients, HLD, and critical micelle concertation (CMC) for alkyl and alkylophenol ethoxylate surfactants. The universal relationship between HLD and activity coefficients is not determined yet, and the relationship changes based on oil, surfactant, and brine properties. HLD has also been used as a quantifiable metric to describe the water-oil-surfactant phase behavior. The effect of pressure on surfactant phase behavior, however, is ignored in the original expression for HLD. Large pressure changes, such as those that occur in enhanced oil recovery applications, increases the affinity of anionic surfactants to brine. Roshanfekr and Johns differentiated the effect of pressure and the change in oil composition as gas is added or evolves from the oil on the phase behavior. They predicted the phase behavior for live oils at high pressures based on experimental measurements of dead oil at atmospheric pressure using a density correlation. Ghosh and Johns recently included a linear term for pressure in HLD that is a more robust and accurate approach.

There is a class of models that have been proposed to predict microemulsion phase behavior that do not depend on specific measures of surfactant affinity, such as HLD. For example, activity coefficients have been estimated from measured data based on Gibbs free energy. Others have used the membrane bending modulus for phase behavior prediction. These models, however, are difficult to extend to real fluids and have not been successful in predicting phase behavior. Thus, this research focuses on the practical approach that relies on HLD as a correlating state function variable.

Acosta et al. advanced the use of HLD when they estimated Gibbs free energy of formation for a micelle based on the net curvature of micelles and correlated the results with the HLD equation and the estimate of average curvature from De Gennes and Taupin. They called the resulting model HLD-NAC (net and average curvature). Later, Acosta used nonionic alcohol ethoxylate and alkylphenol ethoxylate surfactants for oils with varying alkane carbon number (ACN) to develop a correlation for the characteristic length. Acosta fit experimental data from the literature for mixtures of pure surfactants and alkanes. Then, the correlation was used to predict fish diagrams measured by Kunieda and Shinoda.

Although the test data were not used in developing the correlation, the data used for tuning are closely related so that the predictions were within acceptable error. Acosta suggested that a more mechanistic and general correlation of characteristic length is needed to make the HLD-NAC model a true equation-of-state (EoS). Salager et al. demonstrated a strong correlation between surfactant performance and characteristic length. In addition, they studied the effect of different formulation parameters on surfactant performance. They concluded, however, that there is no simple general relationship to predict surfactant performance even for pure surfactants. Ghosh and Johns recently proposed a more practical correlation for characteristic length in type III phase behavior to EACN based on the observed correlation between solubilization ratio at optimum formulation and optimum salinity. Their published correlation is valid as long as only two formulation parameters change simultaneously, one of them being the salinity. With these new correlations, the HLD-NAC model has been successfully used to model many some key properties of real microemulsion phase behavior. The model has become one of the standard surfactant models for benchmarking new thermodynamic developments.

All EoS developments to date with the HLD-NAC model, however, have focused on type III predictions, not type II− and type II+. Catastrophe theory, based on micelle inversion in the type IV region (single-phase region), is used to end the two-phase binodal curve, which would otherwise mistakenly continue to the boundaries of the surfactant-brine and surfactant-oil axis of the ternary diagram. The binodal curve is typically cut at its intersection with a dilution line of constant oil-water ratio, typically 75% for type II− and 25% for type II+ regions. This deficiency in the HLD-NAC model creates discontinuities (see FIG. 1), which can cause significant errors and problems in many applications including numerical simulation. Hence, there is a continuing need for predictive algorithms.

SUMMARY OF THE DISCLOSURE

The present disclosure describes a flash calculation algorithm based on the HLD-NAC model that is consistent for all compositions and phases in a ternary diagram, and therefore eliminates the use of catastrophe theory. The present disclosure extends the HLD-NAC model for type II regions, but not limiting to NAC, based on new physical estimates of the correlation length, and develop a flash calculation algorithm to predict tie lines and tie triangles for all Winsor types (type II−, type II+, type III, and type IV). The new algorithm is completely robust with no iteration required, making it extremely efficient and easy to code.

In sum, the present flash calculation algorithm is an improvement over conventional simulators because: 1) current commercial simulators use Hand's model, which is empirical and unreliable outside the range of experimental data, and 2) the modern and physical based phase behavior models such as HLD-NAC (hydrophylic-lipophylic and net-average curvature) are not consistent over the entire range of formulation variables, and thus could not be used in a simulator or for more general design and predictive use.

These models could also not predict the single- and two-phase regions that often occur in microemulsion phase behaviors that are critical for many applications.

The condition for criticality is given explicitly so that the new flash methodology is completely robust, and very fast. Stability analysis is done first with no iteration required.

The approach eliminates the use of the inaccurate catastrophic theory developed by chemists for the two-phase regions.

The new EoS is tuned to experimental data by varying a new dimensionless group, the I-ratio, and the maximum value of correlation length in the three-phase region. This reduces significantly the number of independent parameters even compared to Hand's method.

One aspect of the method is to allow the three-phase region to be present even though the three-phase region (type III) may not exist in positive composition space. That is, the three-phase region may exist but outside of the ternary diagram.

The approach can predict the phase behavior regions (tie lines and tie triangles, and single-phase regions) away from the measured experimental data.

The formation variables for the flash in the paper include salinity, oil composition (EACN), alcohol, surfactant parameters, temperature and pressure. Other variables can be added to the HLD equation and incorporated in the approach, such as the EON of the surfactant, surfactant tail length, etc.

One additional component of the algorithm is a general way to relate optimum solubility to variation in formulation variables.

The size of the two-phase regions and associated tie lines are physically matched and predicted, and are shown to be significantly impacted by pressure, and other formulation variables.

In accordance with an embodiment of the present disclosure, a non-transitory computer readable recording medium that stores a program having instructions that, when executed by a processor, performs a method of estimating a microemulsion phase composition of surfactant, oil and water is provided. A single-phase region is denoted as Type IV, a three-phase region is denoted as Type III, a two-phase region with time lines having a negative slope is denoted as Type II−, and a two-phase region with time lines having a positive slope is denoted as Type II+. The method may include steps of calculating model parameters based on required input data including at least one of model coefficients, overall composition, salinity, temperature, pressure, and equivalent alkane carbon number (EACN); calculating overall solubilization ratios for the oil and water; determining whether the microemulsion phase composition is in the Type III based on a calculated result of the overall solubilization ratios for the oil and the water; if the microemulsion phase composition is determined to be the Type III, determining a volume fraction of the surfactant in the microemulsion phase composite; and determining a microemulsion phase saturation. The calculated model parameters are further adjusted by a tuning procedure to accurately predict types of phases and the microemulsion phase composition.

The method may further include, if the microemulsion phase composition is not determined to be in the Type III and is determined to be in the Type II+, calculating solubilization ratios for the oil and the water, and determining the volume fraction of the surfactant in the microemulsion phase composition and the microemulsion phase saturation.

The microemulsion phase composition may be determined to be the Type II+ if the determined microemulsion phase saturation is equal to or lower than 1, and it may be determined whether or not the microemulsion phase composition be the Type II+ if the determined microemulsion phase saturation is higher than 1.

The method may further include, if the microemulsion phase composition is not determined to be in the Type III and is determined to be in the Type II−, calculating solubilization ratios for the oil and the water, and determining the volume fraction of the surfactant in the microemulsion phase composition and the microemulsion phase saturation.

The microemulsion phase composition may be determined to be the Type II− if the determined microemulsion phase saturation is equal to or lower than 1, and the microemulsion phase composition may be determined to be the Type IV if the determined microemulsion phase saturation is higher than 1.

The microemulsion phase composition may be determined to be the Type IV if the microemulsion phase composition may not be determined to be in any of the Type III, Type II+, and Type II−.

The tuning procedure of the model parameters may include an initial estimating step of the model parameters and an optimization step to minimize a mean square error between the estimated model parameters and experimental solubilities.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein.

Catastrophe theory creates a singularity in the two-phase regions (from Abbott).

DETAILED DESCRIPTION OF THE DISCLOSURE

Figure 1:
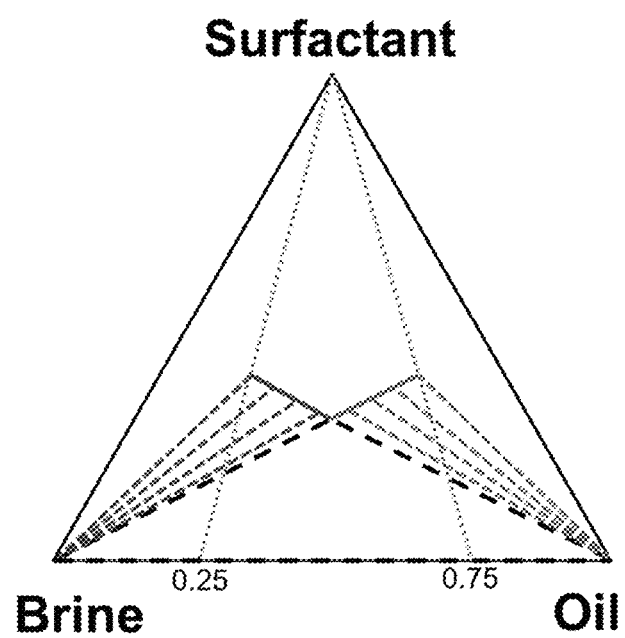
FIG. 1 is a binodal curve that is cut when it reaches a constant value of oil-water ratio, typically 25% for type II+ and 75% for type II−. This creates unphysical discontinuities in compositions and saturations, as the tie lines abruptly end at a single-phase region.

The present flash calculation algorithm is believed to be the first comprehensive flash calculation approach and methodology to use the HLD-NAC equations to estimate the microemulsion phase composition for an overall composition of surfactant, oil, and brine. The oil can be any organic substance, including hydrocarbons and contaminants such as trichloroethylene (TCE). All phase regions (single, two-, or three-phase regions) are determined continuously as a function of composition and other parameters including temperature, pressure, salinity, and so forth. The single-phase region is denoted Winsor type IV, while the three-phase region is denoted type III. Type II− is used to denote the two-phase regions with tie lines that have negative slope, while type II+ is used to denote the two-phase regions with tie lines that have positive slope. Old methods like Hand's empirical model are no longer necessary with the approach.

The following lists the various advantages of the present flash calculation algorithm, which includes:

Robustness and Speed:

1) The condition for criticality is given. Limiting tie lines at critical points are determined analytically.

2) Approach eliminates the use of the inaccurate catastrophic theory for the two-phase regions. The new methodology thereby eliminates composition and saturation discontinuities.

3) The approach requires no iteration and is guaranteed to converge to a solution. Therefore, the technique is fast and robust even compared to the older Hand's model.

4) The approach defines the regions that form without doing a final calculation (stability analysis is done first).

5) The model is tuned based on fitting experimental data by varying the I-ratio and the maximum value of correlation length in the three-phase region. Only two parameters compared to five are used in the tuning process for a standard salinity scan compared to the current state of the art (Hand's model).

6) An important feature in the method is to always allow the three-phase region to be present even though the three-phase region (type III) may not exist in positive composition space. That is, the three-phase region may exist but outside of the ternary diagram. Without this the approach is not possible.

Novel Results:

7) New approach can predict the phase behavior regions (tie lines and tie triangles, and single-phase regions) away from the measured experimental data.

8) The formation variables for the flash in the paper include salinity, oil composition (EACN), alcohol, surfactant parameters, temperature and pressure. Other variables can be added to the HLD equation and incorporated in the approach, such as the EON of the surfactant, etc.

9) Added a parameter to the net average curvature equation to include surfactant volume in the micelle. This parameter (½ factor) can be changed depending on the phase behavior needs (for example if the limiting tie line is critical to the application). The new approach allows for immiscibility between surfactant and either the brine or oil, which could be important for many industrial applications.

10) The sizes of the two-phase regions and optimum solubilities are significantly impacted by pressure, and other formulation variables.

Extensibility:

11) The approach in the disclosure assumes pure excess phases (oil phase is only oil component, and the brine phase is only water and salts). This assumption can be easily relaxed.

12) The present disclosure significantly extends the correlation of Ghosh and Johns (2016) for optimum solubilization ratio as a function of optimum salinity to include other changing formulation variables. The new equations are more general and estimate the maximum correlation parameter as a function of formulation parameters, such as temperature, pressure, and salinity. Other formulation parameters can be used as well.

13) The dimensionless characteristic length parameters are a function of HLD and overall composition for the two-phase regions. The first expression is given to interpolate and obtain this parameter for prediction purposes. The simplest expression is used as possible (an exponential function), but others could be easily used if data warrants. The dimensionless correlation length parameters are assumed constant in the three-phase region, but this could be easily extended to allow for its variation with HLD as an example.

14) The approach is developed using tie-line equations, although other equivalent methods could be used. The extension of the tie line is used to develop continuous predictions from the flash.

15) For a fixed HLD, a linear function is used to interpolate the dimensionless correlation length based on the critical tie-line value of the dimensionless correlation length.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Mathematical Model and Parameters for HLD-NAC

HLD was introduced by Salager et al. as a state function related to excess Gibbs energy of surfactant in the water and oil phases, so that it can be written in differential form as a function of independent variables, $$dH = \sum_i \left.\frac{\partial H}{\partial v_i}\right|_{v_{j\neq i}} dv_i, i = 1, \ldots, DF$$

where H is HLD and $v_i$ is a state variable, and DF is degree of freedom or number of independent state variables. The state variables can include but are not limited to pressure, temperature, water and oil compositions, and surfactant properties. The integration of the above total differential gives the deviation from optimum conditions. Salager et al. correlated HLD to formulation parameters for ionic surfactants, and Ghosh and Johns included a pressure term to the equation. In this paper, the HLD equation for common state function variables is modified to include reference values as, $$H = H_{ref} + \ln\left(\frac{S}{S_{ref}}\right) - K(EACN - EACN_{ref}) + \quad \text{[Equation 1]}$$
$$f(A) + (\sigma - \sigma_{ref}) - \alpha(T - T_{ref}) - \beta(P - P_{ref})$$

where S is the salinity of the aqueous phase (representing the water pseudocomponent), EACN is the equivalent alkane carbon number (representing the oil pseudocomponent), $f(A)$ is a function of the alcohol type and concentration, which should be zero at reference condition, σ is a characteristic parameter representing the surfactant structure, and P is the pressure and ref is at reference conditions, usually obtained at an optimum. Alcohol and surfactant are assumed to partition equally in this paper and are therefore lumped as a pseudocomponent.

Pressure, temperature, EACN and surfactant properties can be adjusted simultaneously to achieve optimum conditions. For non-ionic surfactants and alcohols a linear term is used for salinity. The optimum salinity can be calculated as a function of formulation parameters by setting H to zero, $$\ln S^* = \ln(S_{ref}) + K(EACN^* - EACN_{ref}) - f(A) - (\sigma - \sigma_{ref}) + \alpha(T^* - T_{ref}) + \beta(P^* - P_{ref}) - H_{ref} \quad \text{[Equation 2]}$$

Salager et al. provides a recent review on developments and applications of the HLD concept. For large variation of formulation parameters, the optimum condition has a non-linear relationship with formulation variables. The reference value of HLD in Equation 2 is also set to zero if the reference condition corresponds to an optimum.

Acosta et al. introduced the HLD-NAC model to calculate phase compositions. In the present disclosure, the model is modified to include surfactant component volume in the micelles (see Derivation of modified HLD-NAC equations). The phase compositions for type III can be calculated by solving Equations 22 and 24 together, $$\frac{1}{\sigma_o + 0.5} = \frac{3}{2}I(H^l - H), \text{ and,} \quad \text{[Equation 3]}$$

$$\frac{1}{\sigma_w + 0.5} = \frac{3}{2}I(H^l + H), \quad \text{[Equation 4]}$$

where $H^1 = 2/\xi_D^{max}$. Therefore, the type III region exists when $|H|<H^1$ and the three-phase width in terms of HLD is only dependent on the dimensionless characteristic length of the micelles in our model. The microemulsion phase composition in the type II regions can be calculated based on Equation 24. For type II+, $$\frac{1}{\sigma_w + 0.5} = \frac{6l}{\xi_D} - \frac{1}{\sigma_o^o + 0.5}, \text{ and for type } II-, \quad [\text{Equation 5}]$$

$$\frac{1}{\sigma_o + 0.5} = \frac{6l}{\xi_D} - \frac{1}{\sigma_w^o + 0.5}, \quad [\text{Equation 6}]$$

where $\sigma_o^o$ and $\sigma_w^o$ are overall solubilization ratios that are constant along tie lines, as defined in Section "The characteristic length model in two-phase regions", depending on the type II region. For example, for type II−, the water solubility is constant because water appears only in the microemulsion phase.

Approximating the excess phases as pure oil or water components, the surfactant in microemulsion phase compositions for type II or III regions can be calculated from solubilization ratio where, $$C_s^m = \frac{1}{1 + \sigma_o + \sigma_w}, \quad [\text{Equation 7}]$$

and then, the remaining microemulsion phase compositions and saturations can be calculated directly using, $$S_m = \frac{C_s^m}{C_s}, \quad [\text{Equation 8}]$$

$$C_i^m = C_s^m \sigma_i, \ i = o, w \quad [\text{Equation 9}]$$

$$S_i = C_i - S_m C_i^m, \ i = o, w \quad [\text{Equation 10}]$$

One of the saturations will be zero for the type II regions, e.g. water saturation for type II−, or oil saturation for type II+.

The functional form for solubilities can be summarized as follows when the components are fixed, $\sigma_o, \sigma_w = f(HLD, \eta_D)$ in the three-phase region, and $\sigma_o, \sigma_w = f(HLD, \eta_D, \sigma_{o,w}^o)$ in the two-phase regions, where $\sigma_{w,o}^o$ describes the composition of a component (oil for type II+ or water for type II−) in the microemulsion phase. Other functional forms could be easily used, but the number of dependent variables must be the same (two variables in the three-phase region, and three in the two-phase regions). The current algorithm uses $\sigma_o, \sigma_w = f(HLD, \eta_D = \eta^*_D = \text{constant})$, although it is not limited to this expression.

Flash Algorithm

FIG. 1 is a binodal curve that is cut when it reaches a constant value of oil-water ratio, typically 25% for type II+ and 75% for type II−. This creates unphysical discontinuities in compositions and saturations, as the tie lines abruptly end at a single-phase region. The new flash algorithm in the present disclosure overcomes these limitations.

The new flash calculation methodology for all Winsor types is outlined. The algorithm relies on tie-line parameterization, followed by calculation of the limiting tie lines at the critical point, and then calculation of the correlation length in the two-phase region as a function of HLD and phase composition (see Section "The characteristic length model in two-phase regions").

The method for estimating a microemulsion phase composition of surfactant, oil and water according to an embodiment of the present invention can be tangibly implemented in a non-transitory computer readable recording medium that stores a program of instructions executable by a computer, etc. The non-transitory computer readable recording medium can include each of program instructions, data files and data structures, or a combination of the ones above.

The program of instructions that are written in the non-transitory computer readable recording medium can be specially designed and configured for the present invention, or can be those available, which are generally understood by those of ordinary skill in the field of computer software. The non-transitory computer readable recording medium can be, for example, a hard disk, floppy disk, magnetic media such as magnetic tape, CD-ROM, optical media such as DVD, magneto-optical media such as a floptical disk and hardware device such as a ROM, RAM and flash memory, which are configured to store and perform the program of instructions. In addition to the above, the non-transitory computer readable recording medium can be a program of instructions and a ray of light including a carrier wave that sends a signal specifying the data structure, or can be a transmission medium such as a metal line and waveguide. Examples of the program of instructions can include a machine code, such as those created by a compiler, as well as a high-level language code executable by the computer using an interpreter.

The hardware device mentioned above can be configured to work as one or more of software modules to perform algorithms of the present invention.

Flow Chart

Figure 2:
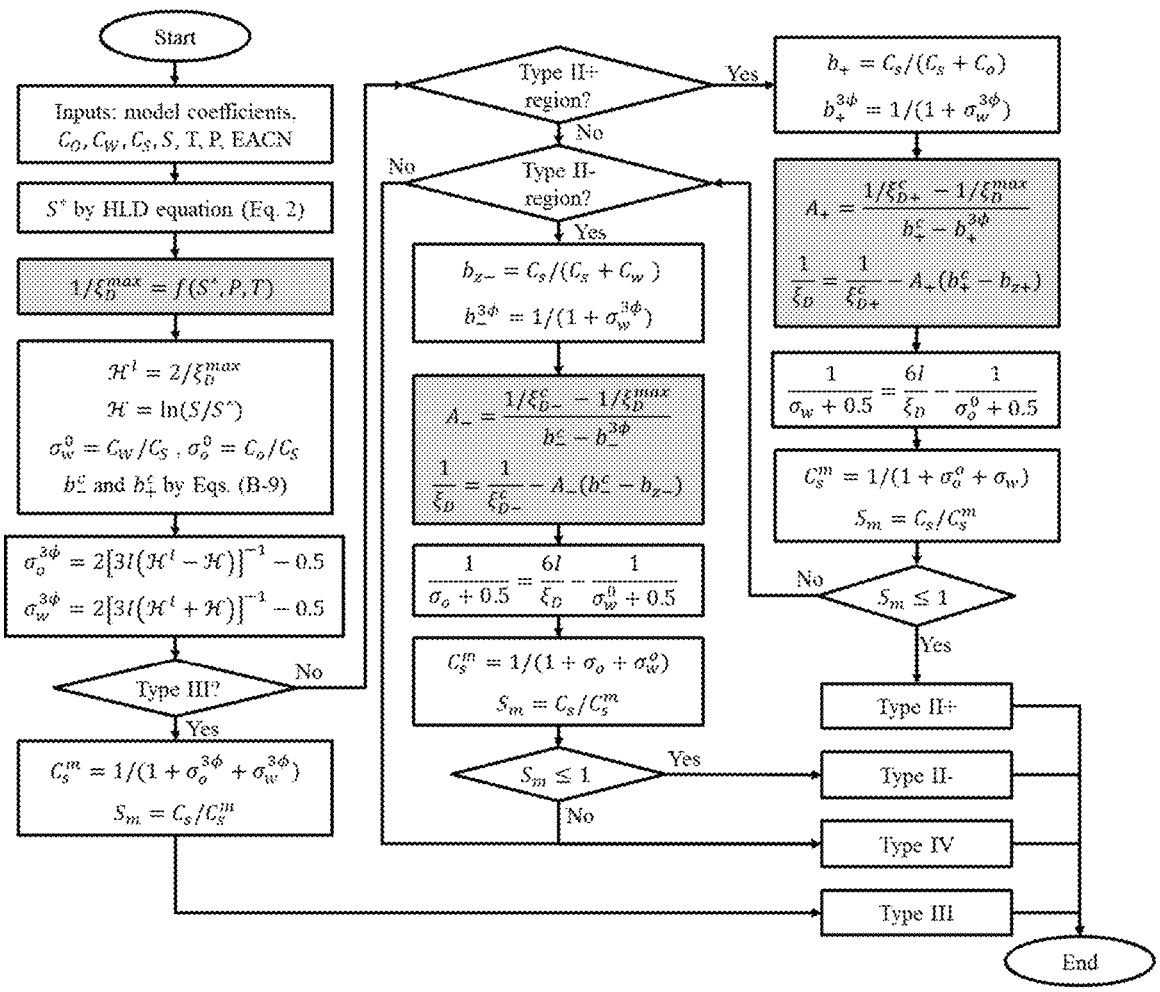
FIG. 2 is a detailed flow chart for the flash calculation algorithm according to an exemplary embodiment of the present disclosure.

A detailed flow chart for the flash calculation algorithm is shown in FIG. 2. The algorithm begins by calculating model parameters based on required input data (model coefficients, overall composition, salinity, temperature, pressure, and EACN). The correlation for solubilization ratio at optimum formulation in this flow chart assumes that only EACN and salinity change. If other formulation variables change, this correlation must be modified as explained earlier. Two examples of such modifications are shown in the results section. Also, the tie-triangle intercepts for each boundary tie line are calculated even when the three-phase region does not exist within the tie triangle, because these values are used to interpolate the characteristic lengths in the two-phase regions. The critical tie lines for each two-phase region can also be inside or outside of the ternary diagram, but they are always used for interpolation.

An important part of any flash algorithm is to identify the number of phases that form at a given overall composition. This is a relatively simple task based on the approach taken here, where tie lines are explicitly defined. Further, the phase types, whether type II−, II+, III, and IV are clearly defined so that there are no phase labeling or identification issues.

Figure 12:
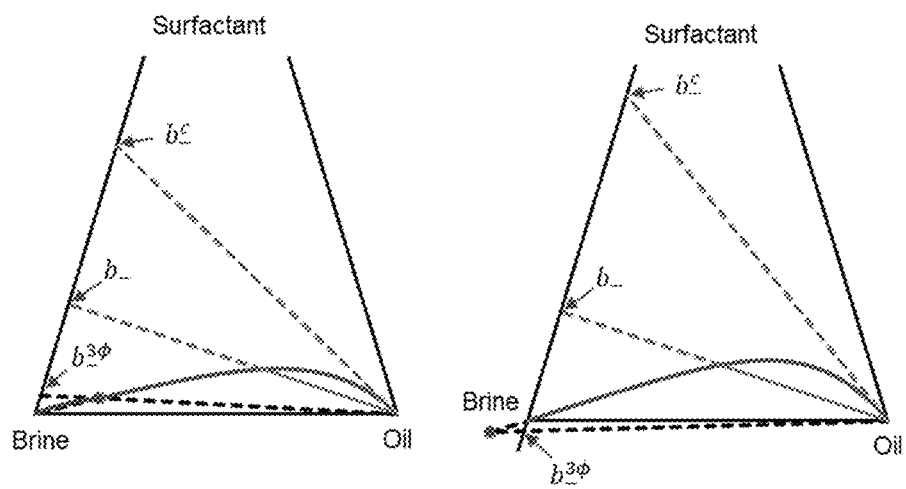
FIG. 12 illustrates an interpolation between a critical tie line and a tie line on the boundary of the three-phase region for type II− according to an exemplary embodiment of the present disclosure.

The extensions of the tie lines for type II+ and type II− intersect inside the ternary diagram. A special case of those tie lines is the tie line that is at the boundary of the three-phase region. These tie lines and their extensions can be calculated whether the phase regions are inside of positive composition space or not. Both the entire three-phase region and part of the two-phase regions can be in negative space (FIG. 12).

The extensions of the tie lines relative to the overall composition differentiates between the existence of two and three phases. A line from any overall composition to each apex is computed and its intersection point ($b_z$) with both the surfactant-water and surfactant-oil axis of the ternary diagram is determined. Further, the microemulsion phase composition is calculated, which determines the tie lines and their extensions (intersection points) at the three-phase boundaries. Thus, the intersection points can be easily compared to determine whether the overall composition lies within the three-phase region. The overall composition is within the three-phase region when, $$|H|<H^1 \text{ and } b_{z+} \leq b_+^{3\phi} \text{ and } b_{z-} \leq b_-^{3\phi} \qquad \text{[Equation 11]}$$

where the condition that $|H|<H^1$ defines when there is a three-phase region inside the ternary diagram (positive microemulsion phase composition as shown in FIG. 26). When the condition is true, the fluid is type III and the flash calculations ends by calculating the microemulsion phase composition and phase saturations. Otherwise, the possibility that the overall composition lies within the type II+ region is checked with the following condition:

$$b_{2+} > b_+^{3\phi} \text{ and } H > -H^1 \text{ and } b_{z+} < b_+^c \qquad \text{[Equation 12]}$$

This condition is satisfied when the overall composition lies between the critical tie line from the type II+ region and the boundary tie line of the tie triangle. Then a negative flash in type II+ is done. If saturations are less than 1.0 the overall composition lies inside the two-phase region for type II+ and the flash calculation ends by estimation of the microemulsion phase saturation and composition. If the conditions are still not met, then the existence of the type II− region is checked with the following conditions, $$b_{z-} > b_-^{3\phi} \text{ and } H < H^1 \text{ and } b_{z-} < b_-^c \qquad \text{[Equation 13]}$$

The condition is satisfied when the overall composition is between the critical tie line and the boundary tie line of the tie triangle. Then a negative flash is done to check whether the overall composition lies within the type II− region. If not, the composition lies within the single-phase type IV region.

Tuning Procedure

The purpose of tuning is to provide a good fit to measured experimental data, but more importantly to generate a model that can predict accurately the amounts and types of phases, and their compositions away from the measured data. A two-step approach is used, where an initial estimate of all fitting parameters is made first, based on simpler plots, and then in a second-step apply automatic fitting to all equations simultaneously so that our resulting model is as unbiased as possible.

In the first step initial estimates of the parameters are made using various plots, depending on what formulation parameters are varied. Some parameters that are not easily calculated can be estimated first by experience, based on averages calculated with other fluids. Some suggested plots for estimating key parameters are given below:

1) A plot of $1/\sigma$ for each component can be used to calculate at least one set of optimums from the intersection point of the water and oil solubilization curves. Based on Equations 3 and 4, the intersection occurs when HLD is zero. The optimum condition can then be used as the reference point for the HLD equation (Equation 2) coefficients.

2) The model for $1/\xi_D^{max}$ and I can be adjusted to match the optimum solubility ratios and width of any measured three-phase region as pressure, salinity, and temperature change.

3) The coefficient of the model for critical tie lines (Equation 31) can be adjusted to match the available two-phase region data.

Once an initial guess of all key fitting parameters are made, conventional optimization techniques can be used to minimize the mean square error between experimental solubilities and predicted values by fine tuning the parameters in Equations 1 and 31, (I and $\xi_D^{max}$). A sufficient set of experimental data must be available to reduce the errors in the estimated fitting parameters and to avoid an underdetermined system. Simultaneous tuning of fluid properties other than phase compositions, such as viscosity and interfacial tension, could significantly help the fluid characterization because these properties are stronger function of micelle shape. If underdetermined, some of the fitting parameters should be assigned, e.g. when pressure and temperature are the only variables in the experimental data, the coefficients $\alpha$, $\beta$ and I are not linearly independent. Further, the adjustment of the tuning parameters by any automatic fitting routine should be inspected to ensure that all parameters remain physical, and ideally should not deviate significantly from the original set of values.

Results

Three different sets of experimental data are used to demonstrate the performance of the new flash algorithm based on the HLD-NAC model. The first two sets consist of measured solubilities where only pressure and temperature vary. The third set is based on solubilities measured at different values of EACN and pressure.

Dead and Live Oil Experiments of Austad and Strand

Austad and Strand measured oil and water solubilization at different pressures and temperatures. Purified $C_{12}$-o-xylene sulfonate at 2.0 wt. % based on aqueous phase was used. The synthetic oil contained 50 wt. % n-decane, 25 wt. %, and 25 wt. % ethylbenzene. The live oil was made by adding methane to the dead oil mixture at high pressure. In contrast to common salinity scans, the salinity is constant in all of these experiments at 2.2 wt. % NaCl. As a result, the optimum salinity is always constant in their experiments and the Ghosh and Johns correlation for solubilization at optimum formulation cannot be used to predict phase behavior with simultaneous changes in only pressure and temperature. Theoretically, temperature or pressure are independent, but the parameter that changes optimum the most in the experimental measurements should be used in fitting. In this example, a better correlation is found, as discussed in Section "The characteristic length model in two-phase regions", when both temperature and pressure were used as follows, $$\frac{1}{\xi_D^{max}} = \beta_1 T + \beta_2 P + \beta_3. \qquad \text{[Equation 14]}$$

TABLE 1

| | Coefficient | Value |
|---|---|---|
| H | $\alpha I$ (° C.$^{-1}$) | $2.1 \times 10^{-3}$ |
| | $T_{ref}$ (° C.) | $5.8 \times 10^{1}$ |
| | $\beta I$ (atm$^{-1}$) | $2.2 \times 10^{-4}$ |
| | $P_{ref}$ (atm) | $2.6 \times 10^{2}$ |
| $\xi_D^{max}$ | $\beta_1$ (° C.$^{-1}$) | $1.2 \times 10^{-1}$ |
| | $\beta_2$ (atm$^{-1}$) | $-1.4 \times 10^{-4}$ |
| | $\beta_3$ (1) | $-3.2 \times 10^{-3}$ |

Figure 3:
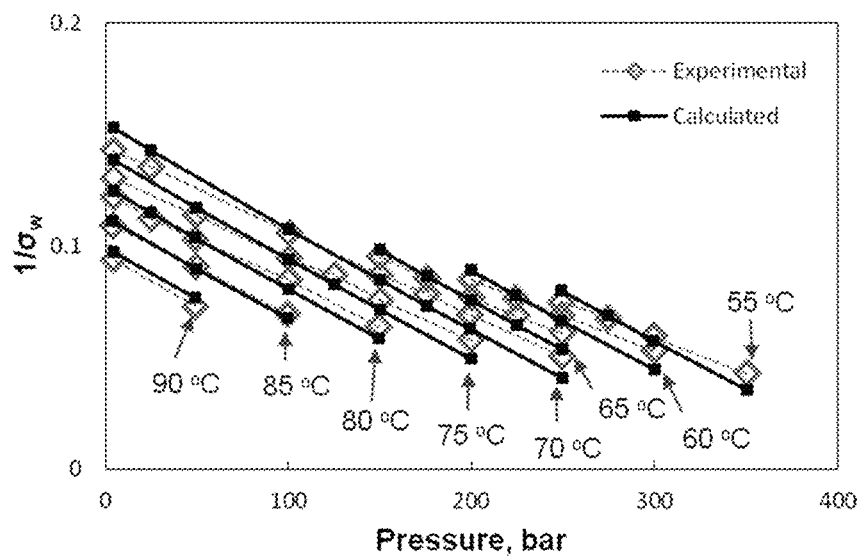
FIG. 3 is a comparison of predicted and fitted data of Austad and Strand using their dead oil experiments. Only experimental data at 65 and 80° C. was used for tuning. The experimental data at 55, 60, 70, 75, 85, and 90° C. are predicted.
Figure 3:
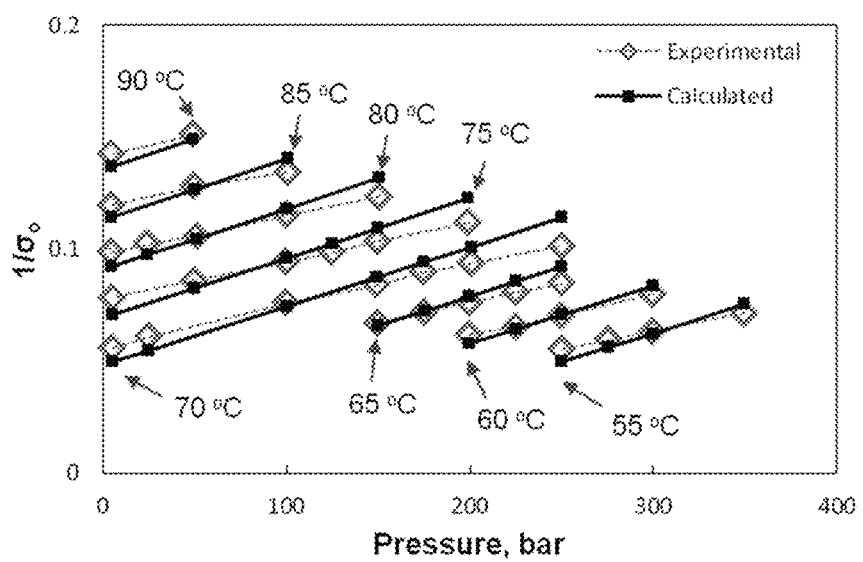

The temperature is varied between 55 and 90° C. for the dead oil experiments. The experimental data at both 65 and 80° C. in the fitting process is used, while other data reported here for different temperatures is predicted. The tuned parameters are given in Table 1. FIG. 3 gives both the predicted and tuned results from the model. The predicted results are excellent. Because salinity does not change in this model, the I-ratio cannot be tuned separately, but rather the group of $\alpha I$ and $\beta I$ are fit.

TABLE 2

| | Coefficient | Value |
|---|---|---|
| H | $\alpha I$ (° C.$^{-1}$) | $1.4 \times 10^{-3}$ |
| | $T_{ref}$ (° C.) | $6.7 \times 10^{1}$ |
| | $\beta I$ (atm$^{-1}$) | $8.3 \times 10^{-5}$ |
| | $P_{ref}$ (atm) | $6.9 \times 10^{2}$ |
| $\xi_D^{max}$ | $\beta_1$ (° C.$^{-1}$) | $1.5 \times 10^{-1}$ |
| | $\beta_2$ (atm$^{-1}$) | $-6.6 \times 10^{-5}$ |
| | $\beta_3$ (1) | $-3.6 \times 10^{-2}$ |

Figure 4:
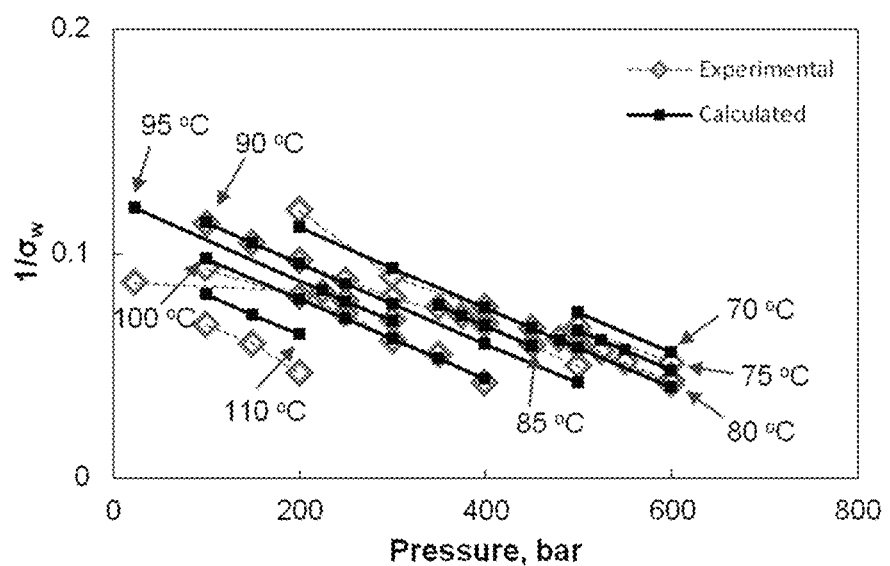
FIG. 4 is a comparison of predicted and fitted data for the live oil experiments from Austad and Strand. Only experimental data at 80 and 100° C. are used for tuning. The experimental data at 70, 75, 85, 90, 95, and 110° C. are predicted.
Figure 4:
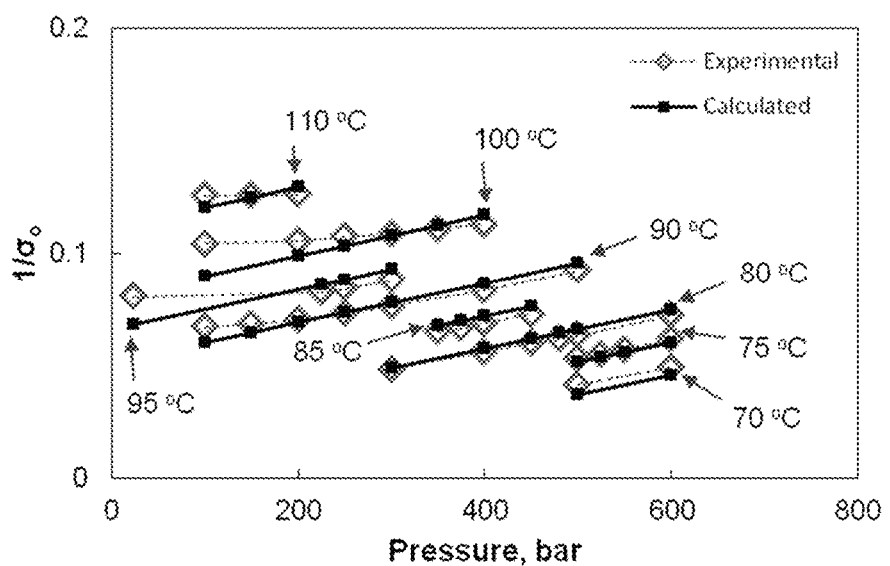

The same procedure for the live experimental data provided by Austad and Strand is repeated. The tuned parameters are given in Table 2, while the comparisons of predicted to experimental data are shown in FIG. 4. Again, the predictions are very good.

Dead and Live Oil Experiments of Roshanfekr et al.

Roshanfekr et al. examined and reported the effect of pressure, EACN, and salinity on microemulsion phase behavior. In this paper, their reported salinity scans are used for octane, decane, and dodecane, dead crude oil A at atmospheric pressure, dead crude oil A, and live crude A (17.7% mol % methane) at high pressure. The temperature was kept constant at 77° F. in the experiments. Isotridecyl propoxylated sulfate (TDA-13PO-SO$_4$) with 27.3 wt % active mater and an internal olefin sulfonate (C$_{15-18}$13PO—SO$_4$) with 27.3 wt % active matter was used as the surfactants. A synthetic mixture of NaCl, CaCl$_2$, MgCl$_2$.6H$_2$O and KCl was used as brine. For these cases, a correlation for solubilization ratio at optimum formulation is used, as discussed in Section "The characteristic length model in two-phase regions", as, $$\frac{1}{\xi_D^{max}} = \beta_1 \ln S^* + \beta_2 P^* + \beta_3 \quad \text{[Equation 15]}$$

The optimum curvature models presented by equations 14 and 15 are two example models. Other equations can be used to predict the optimum curvature without the need to modify the algorithm presented in this paper.

TABLE 3

| | Coefficient | Value |
|---|---|---|
| H | $\beta$ (atm$^{-1}$) | $4.9 \times 10^{-4}$ |
| | $P_{ref}$ (atm) | $3.4 \times 10^{1}$ |
| | K (EACN$^{-1}$) | $1.8 \times 10^{-1}$ |
| | EACN$_{ref}$ (EACN$^{-1}$) | $9.2 \times 10^{0}$ |
| | $S_{ref}$ (wt %) | $2.0 \times 10^{0}$ |
| $\xi_D^{max}$ | $\beta_1$ (1) | $4.3 \times 10^{-2}$ |
| | $\beta_2$ (atm$^{-1}$) | $-3.0 \times 10^{-4}$ |
| | $\beta_3$ (1) | $1.4 \times 10^{-1}$ |
| $\xi_D^{c}$ | $C_1$ (1) | $2.3 \times 10^{1}$ |
| | $C_2$ (1) | $3.2 \times 10^{-2}$ |
| | I (1) | $1.6 \times 10^{-1}$ |

Figure 5A:
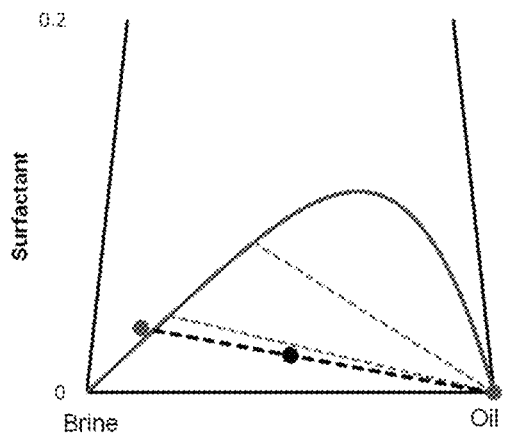
FIGS. 5A-5C are predicted phase diagrams compared to the Roshanfekr and Johns experimental data for live at 1000 psia (dots). The parameter β in HLD equation is estimated based on Roshanfekr and Johns density correlation. The salinities from FIG. 5A to FIG. 5C are 1.32, 1.97 and 3.27 wt %. The overall compositions are shown with black dots.
Figure 5B:
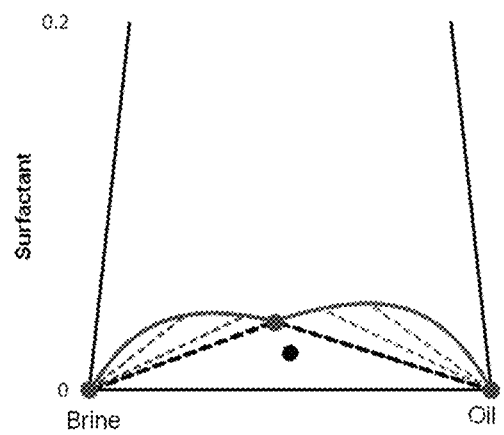
Figure 5C:
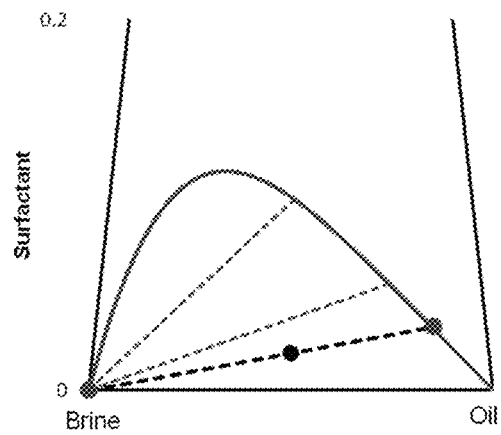
Figure 6A:
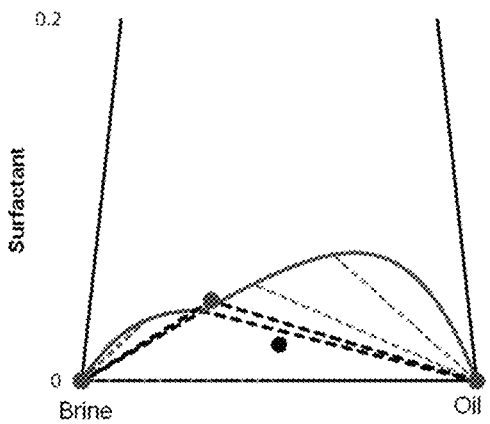
FIGS. 6A-6C are predicted phase diagrams compared to Roshanfekr and Johns experimental data for dead oil at atmospheric pressure (dots). The HLD-NAC parameters are calculated based on Roshanfekr and Johns approach. The salinities from FIG. 6A to FIG. 6C are 1.97, 2.23, and 4.24 wt %. The overall compositions are shown with black dots.
Figure 6B:
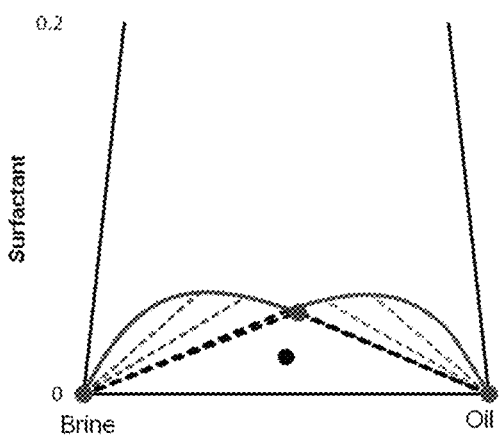
Figure 6C:
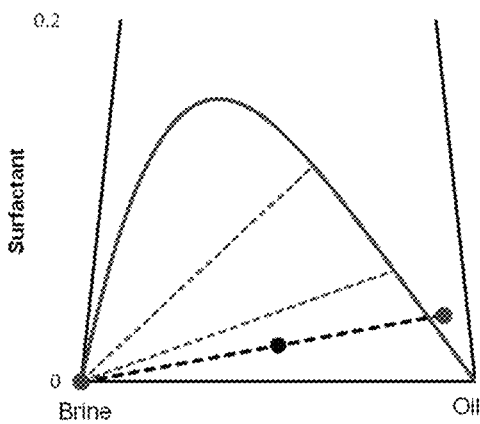

Table 3 gives the values of the fitting parameters based on the tuning coefficients for pressure and EACN in Equation 1. The data set included 46 reported solubilization ratios. FIGS. 5 and 6 give the tie lines and tie triangles predicted from the salinity scan. The predictions and fitted data are excellent. Salinity scans at different water-oil ratio are necessary to improve the two-phase lobe models.

Effect of Pressure on Phase Behavior

Figure 7A:
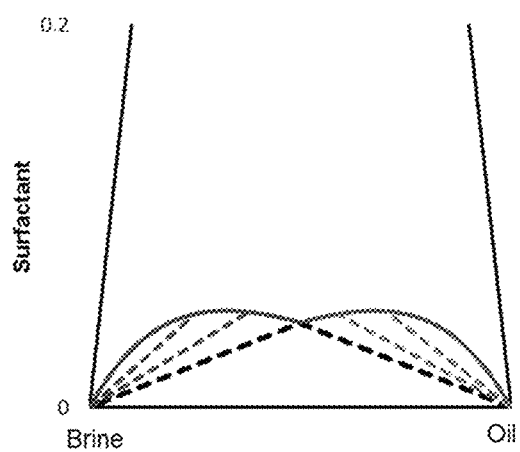
FIG. 7A illustrates an effect of pressure on the three- and two-phase regions based on the experiments with dead oil A from Roshanfekr and Johns at atmospheric pressure and brine with 2.22 wt % salinity.
Figure 7B:
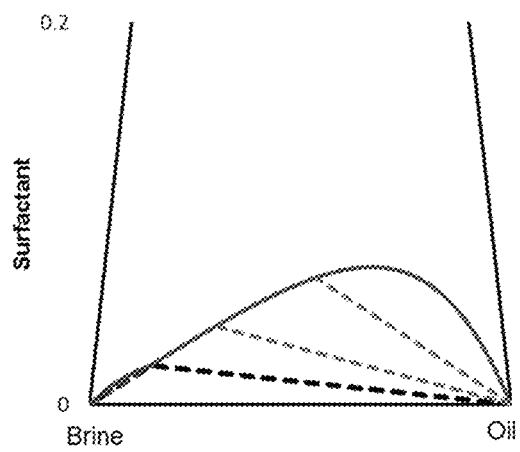
FIG. 7B illustrates an effect of pressure on the three- and two-phase regions based on the experiments with dead oil A from Roshanfekr and Johns at 1000 psia and brine with 2.22 wt % salinity.

There have been few measurements of optimum salinity at high pressure. For a pressure change of 1000 psia, the optimum salinity does not change much, so pressure has often been erroneously ignored. However, this neglects the importance of pressure effect on the two-phase lobes. The effect of pressure on the three-phase region and two-phase lobes based on the tuned model of Roshanfekr et al. are shown in FIG. 7A and FIG. 7B. The three-phase region is shifted somewhat with pressure, but the impact of pressure on the type II– lobe is significant. The impact on optimum solubility is also substantial.

Fish Plots

Figure 8:
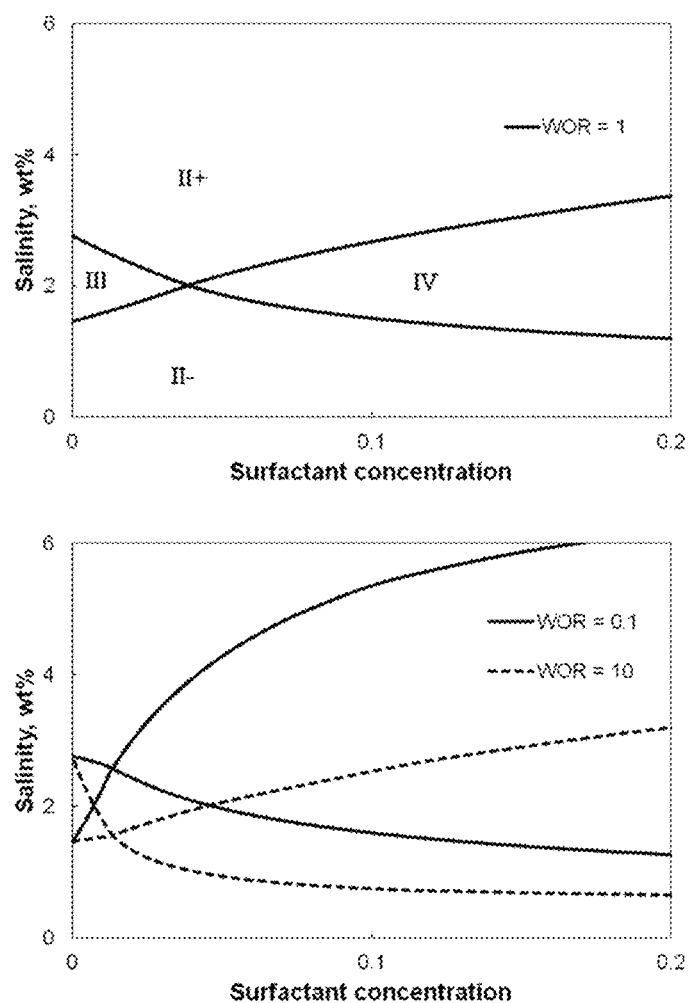
FIG. 8 illustrates predicted fish diagrams for different oil-water ratios with the model tuned to the Roshanfekr and Johns live oil experiments at 1000 psia.

Fish plots can be easily constructed over the entire Winsor region using the new algorithm. For example, predictions of fish plots using the tuned model for the live oil A data from Roshanfekr and Johns is shown in FIG. 8 for three different water oil ratios of 0.1, 1, and 10. The fish diagrams are symmetric for a water-oil ratio of 1.0, but become asymmetric otherwise.

Inclusion of Surfactant Volume in Micelle Radius Calculation

Figure 9A:
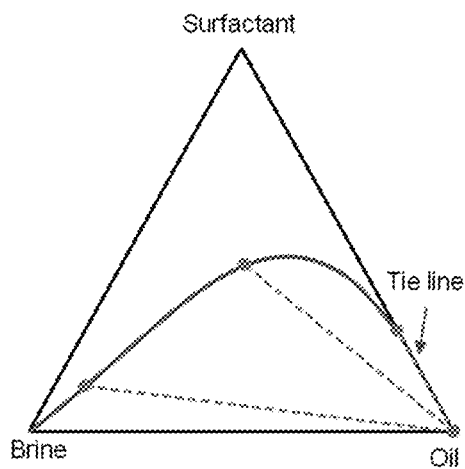
FIGS. 9A-9B are ternary diagrams at large deviation from optimum conditions according to an exemplary embodiment of the present disclosure. H is −1.7 for FIG. 9A and 1.7 for FIG. 9B based on the tuning of data from Roshanfekr and Johns.
Figure 9B:
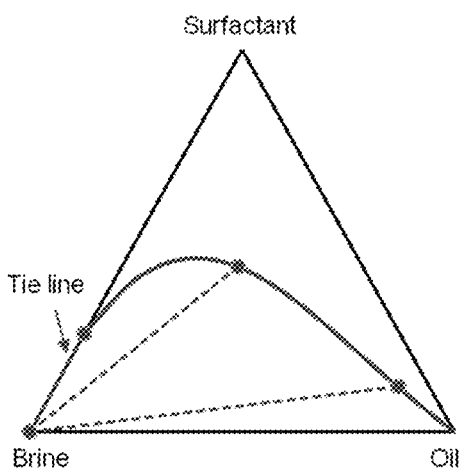

The correction for micelle radii using Equation 17 makes a significant change in the phase behavior when the micelles become small, which occurs away from the three-phase region. FIG. 9 gives an example calculation of the two-phase lobes at large positive and negative HLD. The results show that the critical tie line is no longer inside the ternary diagram, so that the surfactant becomes more immiscible with oil for type II– or water for type II+. The critical tie line is still present, but lies in negative composition space, outside of the ternary diagram. This improvement allows the new algorithm to be applied for conditions away from optimum, as is evidenced in numerous measured experimental data (See Bourrel and Schechter for example).

CONCLUSIONS

The presented disclosure includes the first flash calculation algorithm based on HLD-NAC that can model all Winsor regions. The model assumes spherical micelles and pure excess phases. A detailed flow chart for the algorithm is given, and the results of tuning and prediction were demonstrated for several fluids. Key conclusions are:

1) The dimensionless characteristic length is calculated as a function of HLD and overall composition for the two-phase regions. A new empirical relation is given for correlation length in the two-phase regions that is based on an exponential trend with HLD, but linear interpolation within the two-phase regions at constant HLD.

2) The use of catastrophe theory is eliminated with the new algorithm and replaced with a physical prediction of the two-phase lobes. The proposed model for the two-phase lobes could perhaps be improved further through more comprehensive scanning of tie lines at constant HLD.

3) Immiscibility between surfactant and oil or water is modeled in the new algorithm by accounting for surfactant volume in small micelles.

4) New correlations for solubilization ratio of optimum formulation are developed that allow for variations in any formulation parameter(s). The correlations gave good predictions of solubilization ratios at optimum formulation although a more general and mechanistic relationship for characteristic length is needed in both the two and three-phase zones. In this model, the characteristic length is assumed constant in the three-phase region.

5) The flash is non-iterative and completely robust. Phase labeling and identification are not issues because the limiting tie line at the critical point is calculated directly.

6) The flash calculation results show that pressure shifts the optimum condition and has a significant effect on the size of two phase lobes. Therefore it is important to include pressure in Equation 1 and optimum curvature model. In addition, microemulsion phase behavior must be measured at conditions close to the application process conditions.

Derivation of Modified HLD-NAC Equations to Include Surfactant Volume

The HLD-NAC model is slightly modified here to include the surfactant component volume. Acosta et al. correlated molar excess Gibbs energy of formation for micelles to the radius (or curvature) of micelles. The radii are related to oil and water volumes and surface area of the spherical interface as, $$R_i = \frac{3V_i}{A_s}, \quad i = w, o \quad \text{[Equation 16]}$$

where $V_i$ is the volume of component i in the microemulsion phase, and $A_s$ is the interface surface area.

The contribution of surfactant molecules to the micellar volume has been ignored in current developments of the HLD-NAC model. Based on Acosta et al. model, the energy required to form a micelle with no oil solubility becomes singular and tends to infinity. The oil spheres at the center of micelles that are smaller than a critical radius are unstable causing oil molecules to move to other micelles or become dispersed between surfactant molecule tails. Therefore Equation 16 results in inaccuracies as micelles become small that do not allow for surfactant to become immiscible with oil or water. Experiments show that surfactant is not always miscible with water or oil.

Figure 10:
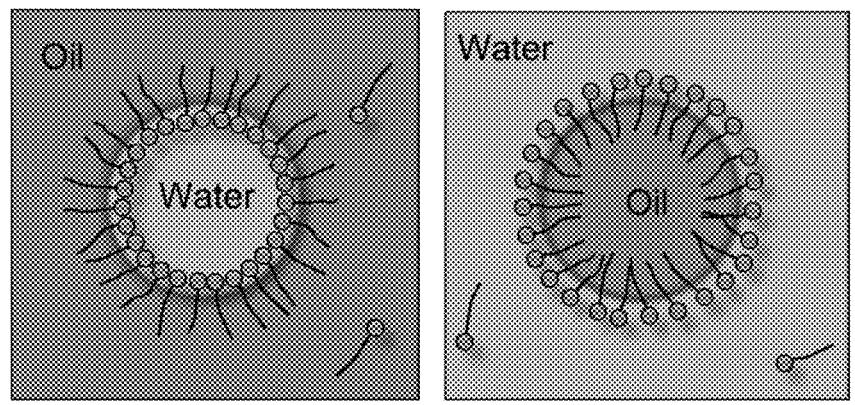
FIG. 10 illustrates a hypothetical interface that encompasses some surfactant volume according to an exemplary embodiment of the present disclosure.

In this paper, a first order correction for this singularity is made and immiscibility is modeled by including the surfactant volume in the micellar volume. For simplicity, it is assumed that the interface cuts the surfactant molecules in half as shown in FIG. 10. The ½ factor could be altered or tuned in future developments based on HLD and/or on whether micelles are inverted or not. The oil and water radius for a micelle can therefore be defined as, $$R_i = \frac{3(V_i + V_s/2)}{A_s}, \quad i = w, o \quad \text{[Equation 17]}$$

where $V_s$ is the surfactant volume.

The ratio between $A_s$ and $V_s$ depends on the shape of micelles and how closely the surfactant molecules are packed in the micelles. Ghosh and Johns defined a new dimensionless parameter called the I-ratio that follows directly from making the HLD-NAC equations dimensionless. The I-ratio closely resembles the packing parameter, and is expressed by, $$I = \frac{V_s}{A_s L} \quad \text{[Equation 18]}$$

where L is the thickness of interface, which is correlated to the surfactant tail length. The I-ratio is therefore the volume of a surfactant molecule in bulk phase (no micelles) divided by the volume of the same surfactant molecule in an aggregate (micelle). The molecular packing parameter is related to the ratio of the surfactant head volume to the tail volume based on thermodynamic equilibrium of micelles. The I-ratio is tuned to experimental data without a detailed understanding of the molecular structure, and is therefore practical for use with real mixtures. A rough analogue of the difference between the packing number and the I-ratio could be made between the alkane carbon number (ACN) and the equivalent alkane carbon number (EACN). That is, the ACN is calculated based on molecular structure, while EACN is determined experimentally by fitting measured data of the oil to linear trends of optimum salinity with proxy fluids.

Equation 17, which assumes spherical packing, can be simplified using I-ratio as, $$R_i = 3IL(\sigma_i + 0.5), \quad i = w, o \quad \text{[Equation 19]}$$

where $\sigma_i$ is the solubility of component i defined as, $$\sigma_i \equiv \frac{C_i^m}{C_s^m}. \quad \text{[Equation 20]}$$

Acosta et al. related net average curvature (NAC) to molar excess Gibbs energy of formation of micelles. They demonstrated that the net curvature ($H_n$) between oil and water micelles in the microemulsion phase is related to HLD, $$H_n = \left(\left|\frac{1}{R_o}\right| - \left|\frac{1}{R_w}\right|\right) = -\frac{H}{L}, \quad \text{[Equation 21]}$$

where $R_o$ and $R_w$ are the radii of coexisting hypothetical spherical aggregates of oil and water, and L is the proportionality constant equal to the length of the surfactant molecule. The net curvature, Equation 21, is therefore related to microemulsion composition using Equation 19, $$\frac{1}{\sigma_o + 0.5} - \frac{1}{\sigma_w + 0.5} = -3/H. \quad \text{[Equation 22]}$$

Equation 22 is not sufficient to calculate $\sigma_o$ and $\sigma_w$. Acosta et al. used the results of De Gennes and Taupin who showed that the flat interface is thermodynamically unstable, and defined the following bound for average curvature, $$H_a = \frac{1}{2}\left(\left|\frac{1}{R_o}\right| + \left|\frac{1}{R_w}\right|\right) \geq \frac{1}{\xi^{max}}, \quad \text{[Equation 23]}$$

where $\xi^{max}$ is the maximum value for characteristic length. The average curvature equation (Equation 23) can be rewritten based on solubilization ratios using Equation 19, $$\frac{1}{\sigma_o + 0.5} + \frac{1}{\sigma_w + 0.5} = \frac{6l}{\xi_D},$$ [Equation 24]

where, the dimensionless characteristic length is defined as, $$\xi_D = \xi/L$$ [Equation 25]

The inequality sign of Equation 23 is dropped by using $\xi_D$ to represent all values of the correlation length away from the maximum. It is assumed for simplicity that $l$ is constant and $\xi_D$ in type III is constant for salinity scans and is equal to $\xi_D^{max}$. The assumption of constant $\xi_D = \xi_D^{max}$ in the three-phase region (type III) is reasonable when the width of the three-phase region is small in terms of changing HLD. The solubilities in Equation 22 and Equation 24 can be calculated for any Winsor region once a model for the characteristic length is defined, as shown in the next section.

The characteristic length model in two-phase regions

Tie Lines:

A line that connects two equilibrium phases is called a tie line. The tie lines in Type II+ are defined as $$C_s = a_+ C_w + b_+ \text{ and for Type II-},$$ [Equation 26]

$$C_s = a_- C_o + b_-$$ [Equation 27]

where a and b are calculated assuming that excess phases are pure:

$$a_+ = -\frac{1}{1+\sigma_o^o}, b_+ = -a_+$$ [Equation 28]

$$a_- = -\frac{1}{1+\sigma_w^o}, b_- = -a_-$$ [Equation 29]

Figure 11:
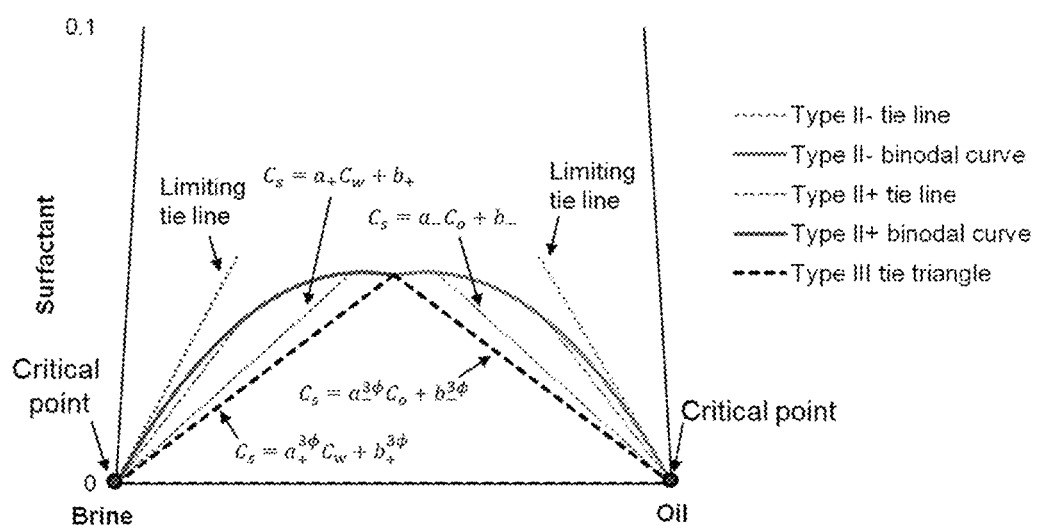
FIG. 11 is a phase diagram having critical tie lines based on tie-line equations for type II+ and II− according to an exemplary embodiment of the present disclosure.

The parameter α is the slope of the tie line, while b is the intersection of the tie line with the ternary axis where either oil (for type II-), or water overall composition (for type II+) is zero. Parameterization of the tie lines is used to define a relationship for $\xi_D$. The tie-line space parameter is defined based on overall composition so that no iteration is required in the flash calculations. The two-phase regions are bounded by critical tie lines that emanate from the oil and water apex of the ternary diagram. An example type III tie triangle is shown in FIG. 11, along with its associated two-phase lobes (type II+ on the left and type II- on the right) and limiting tie lines. The ternary diagram of FIG. 11 is stretched for clarity at small surfactant concentrations.

Critical Points:

The analytical calculation of the limiting tie lines as each critical point is approached (called the critical tie line) is the key to developing a continuous transition between the two phase and supercritical regions, and avoiding the use of catastrophe theory (see FIG. 1). The critical points exist where the equilibrium phase compositions become equal. Because the excess phases are always pure in this model, the critical points must therefore occur at the oil and water apex of the phase diagram, as shown in FIG. 11. A small two-phase oil-water region must exist below the tie triangle, but this region occurs at small surfactant concentrations and is ignored here for simplicity. Current reservoir simulators generally approximate this small two-phase region by the critical micelle concentration (CMC), so that there is no micellar phase if the surfactant concentration is less than the CMC.

All tie lines in the two-phase regions have slopes given by Equations 28 and 29. Further, they are dilution lines of constant ratio $\sigma_i = C_i^m/C_s^m$. The critical tie lines are limiting cases of these tie lines and are tangent to the two-phase region when $C_s^m = 0$. Thus, from Equation 24, the criticality condition becomes, $$\frac{6l}{\xi_D^c} = \frac{1}{\sigma_i^c + 0.5}, i = o, w$$ [Equation 30]

where for type II- is brine and the correlation length equals $\xi_{D-}^c$ while for type II+ component is oil and $\xi_{D+}^c$. The superscript c denotes criticality.

Equation 30 relates the critical correlation length to the limiting value of phase j solubility. For positive values of critical solubilities, there is a single-phase region to the right or left of the limiting tie line (a supercritical region). When $\sigma_w^c$ is calculated to be negative, surfactant is not miscible with water, and similarly for negative $\sigma_o^c$, surfactant is not miscible with oil. That is, for negative solubility there is no critical tie line inside the ternary diagram, but it is mathematically present outside the diagram.

Determination of Characteristic Length

The characteristic length is required to predict phase compositions for all Winsor types. For the three-phase region, the characteristic length should be a function of HLD, but for simplicity $\xi_D = \xi_D^{max}$ is used for salinity scans. The correlation of Ghosh and Johns is modified to include the variation of multiple formulation parameters. Several examples of these relationships are given in the results section.

The characteristic length in a two-phase region should be a function of two parameters owing to an increase of one degree of freedom. Like the three-phase region (tie triangles), every tie line has one value of the characteristic length. The characteristic length is taken to be a function of HLD and solubility of one component. Thus, for type II-, $\xi_D = f(H, \sigma_w^o)$ and for type II+, $\xi_D = f(H, \sigma_o^o)$. For consistency, the correlation length in the two-phase zones must equal $\xi_D^{max}$ at the boundary of the three-phase region. In addition, to ensure that the solution remains bounded, the characteristic length for the critical tie line is expressed as a function of HLD. Thus, $\xi_D^c = \xi_D^{max}$ when the microemulsion phase composition is either at the oil or water apex. This occurs when the three-phase zone vanishes at $H \equiv H^{\pm}$ as defined previously.

The simplest model for the critical tie-line correlation length for type II- that satisfies all required limits is, $$\frac{1}{\xi_{D-}^c} = C_1\left(1 - e^{C_2(H-H^1)}\right) + \frac{1}{\xi_D^{max}},$$ [Equation 31]

where $C_1$ and $C_2$ are fitting parameters based on available data. A similar function is used for the type II+ region. Equation 31 is selected based on the general trend of experimental data. The exponential function is used to ensure that the correlation length approaches a finite value at large positive or negative HLD. Experiments have shown that micelle radii approach a small value at very large deviation from optimum. More experimental data can be used to improve Equation 31 for more accurate predictions.

Linear interpolation of the dimensionless correlation length in the two-phase regions is used based on the critical tie-line value of the dimensionless correlation length. That is, for type II-, $$\frac{1}{\xi_D} = \frac{1}{\xi_{D-}^c} - A_-(b_-^c - b_-),$$ [Equation 32]

where $A_-$ is calculated as $$A_- = \frac{\frac{1}{\xi_{D-}^c} - \frac{1}{\xi_D^{max}}}{b_-^c - b_-^{3\phi}},$$ [Equation 33]

and the critical tie-line intercept with the surfactant-brine axis is given by, $$b_-^c = \frac{1}{1 + \sigma_w^c}.$$ [Equation 34]

A similar equation can be written for the type II+ region, but the intercept is along the surfactant-oil axis of the ternary diagram. Further, a quadratic equation could be obtained from the above expressions to calculate the critical oil and water solubility analytically using the positive root. A more complex function for interpolation of $\xi_D$ in the two-phase region could be used if desired and warranted based on experimental data.

The two-phase solubilization ratios can be used to calculate the coefficient for interpolating tie lines. The parameter $A_-$, which is necessary for interpolation of $\xi_D$ in type II− can be calculated from experimental data using Equation 32. The values of $\xi_D^{max}$ and $b_-^{3\phi}$ are needed, which can be calculated based on three-phase solubilization ratios.

Given $A_-$, the critical tie line can be calculated analytically and the parameters in Equation 31 can be tuned. When multiple two-phase data points are available at the same HLD, the average value of $A_-$ can be used. The parameters $b_-^c$ from Equation 34 and $\xi_{D-}^c$ from Equation 30 are substituted into Equation 33. The result is a quadratic equation for $\sigma_w^c$ as $$(6I)\sigma_w^{c2} + \left(9I - \frac{1}{\xi_D^{max}} - A_- b_-^{3\phi}\right)\sigma_w^c - \left(\frac{1}{\xi_D^{max}} + A(1 + b_-^{3\phi})\right) = 0$$ [Equation 35]

The root that is greater than −0.5 is the physical root for the critical tie line. The −0.5 comes from the use of ½ in Equation 17.

The tie-line parameter b is used for interpolation because it is always continuous and is constant for each tie line. The interpolation can be used even when the three-phase region disappears from positive composition space on the ternary diagram. FIG. 12 demonstrates this for two cases; one where a three-phase region exists inside the diagram, and another where it occurs in negative composition space.

Figure 13:
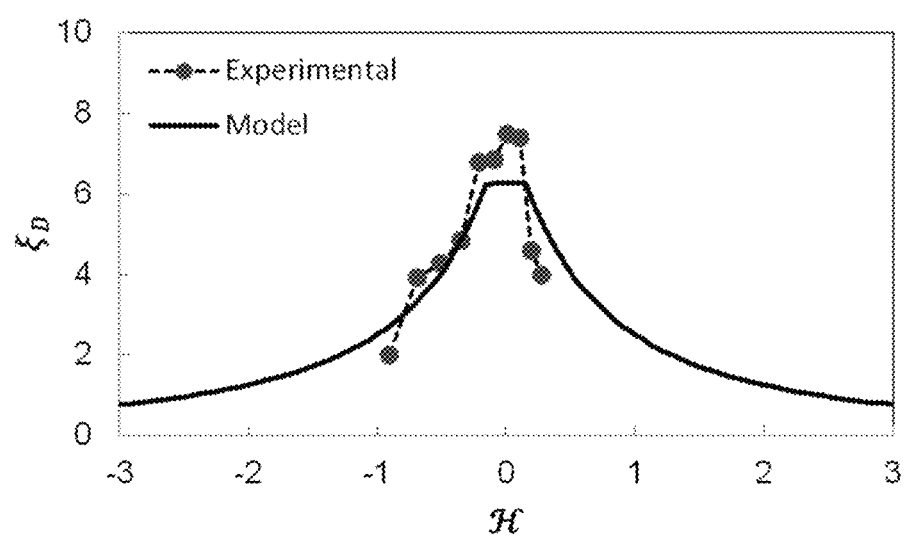
FIG. 13 illustrates example of calculated values of the dimensionless characteristic length for the octane system in Roshanfekr and Johns.

The resulting characteristic length will be as shown in FIG. 13, where it is calculated from the experimental data of Roshanfekr and Johns. The trend of characteristic length shown is consistent with experimentally measured values after tuning. FIG. 13 shows that the assumption of a constant characteristic length in the three-phase region is reasonable, but not precise. That assumption biases the fit of the data, and ideally should be eliminated in a future algorithm.

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

Nomenclature

A=Characteristic length interpolation coefficient
a=Tie-line slope
ACN=Alkane carbon number
$A_s$=Interface area
b=Tie-line intercept
C=Volume fraction
C=Coefficient for critical characteristic length
DF=Degree of freedom
EACN=Equivalent alkane carbon number
$f(A)$=function of the alcohol type and concentration
H=Hydrophilic-Lipophilic difference
HLD=Hydrophilic-Lipophilic difference
H=Curvature
I=I-ratio
K=EACN coefficient in HLD equation
L=Length scaling parameter
p=Pressure, atm
R=Micelle radius
S=Salinity, wt %
S=Phase saturation
T=Temperature, ° C.
v=State variable
V=Component volume in microemulsion
α=Temperature coefficient in HLD equation, ° C.$^{-1}$
β=Pressure coefficient in HLD equation, atm$^{-1}$
β=Characteristic length coefficients
ξ=Characteristic length
σ=characteristic parameter representing the surfactant structure
σ=Solubilization ratio
Superscripts
*=Optimum formulation
3φ=Three phase
c=Critical
l=HLD limit for positive three phase
m=Microemulsion
max=Maximum
o=Overall
Subscripts
−=Type II−
+=Type II+
a=Average
D=Dimensionless
i=Index for state variable, phase, or component
n=Net
o=Oil
ref=At reference condition
s=Surfactant
w=Water
z=Overall composition

What is claimed is:

1. A method of estimating a microemulsion phase composition of surfactant, oil and water in which a single-phase region is denoted as Type IV, a three-phase region is denoted as Type III, a two-phase region with time lines having a negative slope is denoted as Type II−, and a two-phase region with time lines having a positive slope is denoted as Type II+, the method comprising steps of:
- receiving required input data including at least one of model coefficients, overall composition, salinity, temperature, pressure, and equivalent alkane carbon number (EACN);
- calculating model parameters based on the received required input data;
- calculating overall solubilization ratios for the oil ($\sigma_o^{3\Phi}$) and water ($\sigma_w^{3\Phi}$) according to Equations, $\sigma_o^{3\Phi}=2[3I(\mathcal{H}^{-1}-\mathcal{H})]^{-1}-0.5$ and $\sigma_w^{3\Phi}=2[3I(\mathcal{H}^{-1}+\mathcal{H})]^{-1}-0.5$, respectively, where $3\phi$ is a three phase, $\mathcal{H}$ is a hydrophilic lipophilic difference (HLD), and I is an interfacial volume ratio;
- where parameters in the Equations are determined by $$\ln S^* = \ln(S_{ref}) + K(EACN^* - EACN_{ref}) -$$
$$f(A) - (\sigma - \sigma_{ref}) + \alpha(T^* - T_{ref}) + \beta(P^* - P_{ref}) - H_{ref},$$
$$\mathcal{H}^1 = 2/\xi_D^{max}, \frac{1}{\xi_D^{max}} = \beta_1 \ln S^* + \beta_2 P^* + \beta_3, \mathcal{H} = \ln(S/S^*),$$
$$\sigma_w^0 = C_W/C_S, \sigma_o^0 = C_O/C_S,$$

where S is salinity, K is an EACN coefficient, $f(A)$ is a function of alcohol type and concentration, σ is a solubilization ratio, α is a temperature coefficient, T is temperature, β is a pressure coefficient, P is pressure, H is an average curvature, ξ is a characteristic length, C is a volume fraction;
- determining whether the microemulsion phase composition is in the Type III based on a calculated result of the overall solubilization ratios for the oil and the water; and
- if the microemulsion phase composition is determined to be the Type III, determining a volume fraction of the surfactant in the microemulsion phase composition ($C_s^m$) according to Equation A $$C_s^m = \frac{1}{1 + \sigma_o + \sigma_w}, \qquad \text{Equation A}$$

and
- determining a microemulsion phase saturation ($S_m$) according to Equation B $$S_m = C_g/C_g^m \qquad \text{Equation B,}$$

wherein the calculated model parameters are further adjusted by a tuning procedure to accurately predict types of phases and the microemulsion phase composition.

2. The method of claim 1, further comprising:
if the microemulsion phase composition is not determined to be in the Type III and is determined to be in the Type II+, calculating solubilization ratios for the oil and the water according to Equation C, $$\frac{1}{\sigma_w + 0.5} = \frac{6I}{\xi_D} - \frac{1}{\sigma_o^o + 0.5}, \qquad \text{Equation C}$$

where I is an I-ratio and $\xi_D$ is a dimensionless characteristic length, wherein $\xi_D$ is determined by $$b_{z-} = C_s/(C_s + C_w), b_-^{3\phi} = 1/(1 + \sigma_w^{3\phi}), \text{ and}$$
$$\frac{1}{\xi_D} = \frac{1}{\xi_{D-}^{cc}} - A_-(b_-^c - b_{z-}),$$

where $b_z$ is an intersection point, A is a characteristic length interpolation coefficient; and
- determining the volume fraction of the surfactant in the microemulsion phase composition and the microemulsion phase saturation according to the Equation A and the Equation B, respectively.

3. The method of claim 2, wherein the microemulsion phase composition is determined to be the Type II+ if the determined microemulsion phase saturation is equal to or lower than 1, and it is determined whether or not the microemulsion phase composition be the Type II+ if the determined microemulsion phase saturation is higher than 1.

4. The method of claim 3, further comprising:
if the microemulsion phase composition is not determined to be in the Type III and is determined to be in the Type II−, calculating solubilization ratios for the oil and the water according to Equation D, $$\frac{1}{\sigma_o + 0.5} = \frac{6I}{\xi_D} - \frac{1}{\sigma_w^o + 0.5}, , \qquad \text{Equation D}$$

and
- determining the volume fraction of the surfactant in the microemulsion phase composition and the microemulsion phase saturation according to the Equation A and the Equation B, respectively.

5. The method of claim 4, wherein the microemulsion phase composition is determined to be the Type II− if the determined microemulsion phase saturation is equal to or lower than 1, and the microemulsion phase composition is determined to be the Type IV if the determined microemulsion phase saturation is higher than 1.

6. The method of claim 5, wherein the microemulsion phase composition is determined to be the Type IV if the microemulsion phase composition is not determined to be in any of the Type III, Type II+, and Type II−.

7. The method of claim 1, wherein the tuning procedure of the model parameters includes an initial estimating step of the model parameters and an optimization step to minimize a mean square error between the estimated model parameters and experimental solubilities.

* * * * *